(12) United States Patent
Sato

(10) Patent No.: US 9,035,240 B2
(45) Date of Patent: May 19, 2015

(54) ION TRANSFER DEVICE

(75) Inventor: Tomoyoshi Sato, Tsukuba (JP)

(73) Assignee: ATONARP INC., Hachioji-Shi, Tokyo (JP)

( * ) Notice: Subject to any disclaimer, the term of this patent is extended or adjusted under 35 U.S.C. 154(b) by 0 days.

(21) Appl. No.: 13/820,026

(22) PCT Filed: Aug. 31, 2011

(86) PCT No.: PCT/JP2011/004890
§ 371 (c)(1),
(2), (4) Date: Jul. 12, 2013

(87) PCT Pub. No.: WO2012/029315
PCT Pub. Date: Mar. 8, 2012

(65) Prior Publication Data
US 2013/0284916 A1    Oct. 31, 2013

(30) Foreign Application Priority Data

Aug. 31, 2010 (JP) ................................. 2010193382
Oct. 29, 2010 (JP) ................................. 2010243961

(51) Int. Cl.
*H01J 49/04* (2006.01)
*H01J 49/22* (2006.01)
(Continued)

(52) U.S. Cl.
CPC .............. *H01J 37/08* (2013.01); *G01N 27/624* (2013.01); *H01J 49/022* (2013.01); *H01J 49/04* (2013.01); *G01N 1/38* (2013.01); *G01N 2001/2893* (2013.01)

(58) Field of Classification Search
CPC ....... H01J 49/06; H01J 49/062; H01J 49/065; H01J 49/066; H01J 49/40; H01J 49/401; H01J 49/403; H01J 49/408

USPC .................................................. 250/281–283
See application file for complete search history.

(56) References Cited

U.S. PATENT DOCUMENTS

2003/0132379 A1\*  7/2003  Li .................................. 250/286
2006/0192102 A1\*  8/2006  Miller et al. ................... 250/286
(Continued)

FOREIGN PATENT DOCUMENTS

JP       2008-508693 A    3/2008
WO    WO 2006/013396 A2    2/2006
(Continued)

OTHER PUBLICATIONS

International Search Report (PCT/ISA/210) issued on Dec. 6, 2011, by the Japanese Patent Office as the International Searching Authority for International Application No. PCT/JP2011/004890.

*Primary Examiner* — Michael Logie
*Assistant Examiner* — David E Smith
(74) *Attorney, Agent, or Firm* — Buchanan Ingersoll & Rooney PC (57) ABSTRACT

There is provided a transfer device (30) that transfers ionized substances in a first direction. The transfer device (30) includes a drift tube (50) and the drift tube (50) includes electrode plates (71) and (72) constructing an outer wall and a plurality of ring electrodes (60, 61, 62) disposed inside the tube. The ring electrodes (60) forms a first AC electric field for linear driving that causes the ionized substances to travel in the first direction that is the axial direction. The electrode plates (71) and (72) form an asymmetric second AC electric field that deflects the direction of travel of the ionized substances.

13 Claims, 9 Drawing Sheets

(51) Int. Cl.
*H01J 37/08* (2006.01)
*G01N 27/62* (2006.01)
*H01J 49/02* (2006.01)
*G01N 1/38* (2006.01)
*G01N 1/28* (2006.01)

(56) References Cited

U.S. PATENT DOCUMENTS

| | | |
|---|---|---|
| 2009/0114812 A1* | 5/2009 | Landgraf .................. 250/282 |
| 2010/0314548 A1 | 12/2010 | Munchmeyer et al. |
| 2010/0327157 A1* | 12/2010 | Green et al. ............... 250/282 |
| 2011/0006196 A1 | 1/2011 | Boyle et al. |
| 2011/0036977 A1 | 2/2011 | Denton et al. |
| 2011/0114835 A1 | 5/2011 | Chen et al. |
| 2011/0186724 A1* | 8/2011 | Nolting et al. ............. 250/282 |
| 2011/0204221 A1 | 8/2011 | Satake et al. |
| 2011/0266435 A1* | 11/2011 | Hoyes et al. .............. 250/282 |
| 2011/0291001 A1 | 12/2011 | Hoyes et al. |
| 2012/0312981 A1* | 12/2012 | Imai ........................ 250/282 |

FOREIGN PATENT DOCUMENTS

| | | |
|---|---|---|
| WO | WO 2009/089818 A1 | 7/2009 |
| WO | WO 2009/094059 A2 | 7/2009 |
| WO | WO 2009/147411 A2 | 12/2009 |
| WO | WO 2010/020763 A2 | 2/2010 |
| WO | WO 2010/044370 A2 | 4/2010 |

* cited by examiner

ION TRANSFER DEVICE

TECHNICAL FIELD

The present invention relates to a device that transfers ionized substances.

BACKGROUND ART

In recent years, apparatuses called FAIMS (Field Asymmetric Ion Mobility Spectrometers) have been subject to attention as a technology for detecting and analyzing chemical substances with high sensitivity. Such apparatuses use a minute filter to detect changes in mobility of ionized chemical substances caused by changes in a DC voltage and an AC voltage applied to a sensor and are capable of specifying chemical substances according to the differences in the detection results.

Japanese Patent Publication No. 2008-508693 (WO2006/013396) discloses an ion mobility spectrometer having an ion filter in the form of at least one ion channel with a plurality of electrodes. With this ion mobility spectrometer, it is possible for a filler to selectively admit ion species according to a time-varying potential that is applied to conductive layers. Such potential has a drive field component and a transverse field component, and in a preferred embodiment, the respective electrodes contribute to the generation of components of both the drive field and the transverse field. Such device may be used even without a drift gas flow.

DISCLOSURE OF THE INVENTION

FAIMS (Field Asymmetric waveform Ion Mobility Spectrometry) and DIMS (Differential Ion Mobility Spectrometry) are known as technologies that measure ion mobility. FAIMS technology ionizes chemical substances to be measured and uses the property that ion mobility is unique to each chemical substance. While moving such substances in a carrier gas (buffer gas), a differential voltage (or "DV", "Dispersion Voltage", "Vd voltage", "AC voltage", "electric field voltage Vrf", hereinafter simply "Vf") and a compensation voltage (or "CV", "Vc voltage", "compensation voltage", "DC voltage", hereinafter simply "Vc") are changed to alternately and asymmetrically switch between a high electric field and a low electric field. By doing so, during flight, chemical substances aside from target substances collide with the electrodes (plates) that generate the electric fields, lose their electric charge, and are not detected. On the other hand, if the conditions of the voltage Vf and the voltage Vc are appropriately controlled, ionized chemical substances that are the detection target will reach a detector and can be detected as currents flowing in the detector.

One aspect of the present invention is a transfer device that transfers ionized substances in a first direction. Such transfer device includes: a plurality of first electrodes that are aligned in the first direction, regularly reverse a direction of an electric field formed between at least some adjacent electrodes out of the plurality of first electrodes, and form a first alternating current (AC) electric field for linear driving that causes at least some of the ionized substances to travel in the first direction; and a plurality of second electrodes that are aligned in a second direction that differs to the first direction and forms a second alternating current (AC) electric field that is asymmetric and deflects a direction of travel of at least some of the ionized substances in the second direction.

In this transfer device, the direction of an electric field formed between at least some adjacent electrodes out of the plurality of first electrodes is regularly reversed. Typically, the plurality of first electrodes are switched so as to regularly (i.e., in short cycles) reverse the polarities of adjacent electrodes. Accordingly, a first AC electric field for linear driving is formed by the plurality of first electrodes and the plurality of first electrodes function as a linear electrostatic motor for the substances. The first direction may be straight or may be curved.

The average movement velocity vd of an ion in an electric field is given by Equation (1) below.

$$vd = KE \qquad (1)$$

Here, E is the strength of the electric field and K is the mobility (ion mobility), which is a parameter that is unique for each chemical substance (molecule, atom, gas constituent, composition, or the like). Accordingly, chemical substances that match (or are synchronized with) the conditions of the first AC electric field, which include the ion mobility, the strength of the electric field, and the switching rate (frequency), are transferred in the first direction and outputted from the transfer device. Also, since the concentration of chemical substances that match (or are synchronized with) the conditions of the first AC electric field falls in the transfer device, such chemical substances are effectively drawn into the transfer device.

As shown by FAIMS technology, the asymmetric second AC electric field formed by the plurality of second electrodes aligned in the second direction causes chemical substances whose ion mobility matches the conditions of the second AC electric field to remain within the second electrodes. Accordingly, in this transfer device, chemical substances that match the conditions of the second AC electric field remain between the second electrodes and if such chemical substances match the conditions of the first AC electric field, the chemical substances are transferred at high speed in the first direction. This means that it is possible to provide a transfer device that has high selectivity and is capable of efficiently transferring specified chemical substances, even in trace amounts.

Although a high electric field strength is required to form a first AC electric field that is capable of linear electrostatic driving, by narrowing the distances between the plurality of first electrodes using micromachining or MEMS technology, it is possible to transfer ionized chemical substances without using an extremely high voltage. It is also possible to provide a compact transfer apparatus.

The plurality of first electrodes should preferably be disposed within the second AC electric field formed by the plurality of second electrodes. As one example, the plurality of first electrodes may include a plurality of ring-shaped electrodes that are disposed in a line in the first direction substantially midway between two facing electrodes that are included in the plurality of second electrodes. In addition, the two facing electrodes included in the plurality of second electrodes should preferably form a cylindrical flow path and the plurality of ring-shaped electrodes should preferably be disposed along a center axis of the cylindrical flow path. One example of the second AC electric field includes an alternating current (AC) component and a direct current (DC) component.

Another aspect of the present invention is an apparatus (ion mobility sensor, detection apparatus, measuring apparatus) including: the transfer device (transfer apparatus) described above; an ionizing unit that ionizes substances to be introduced into the transfer device; and a detector that detects substances ejected from the transfer device. The transfer device feeds chemical substances that match the conditions of the first AC electric field and the second AC electric field to the detector. Accordingly, it is possible to provide an ion mobility sensor with high separation performance (i.e., resolution) and a detection apparatus that uses such ion mobility sensor. With such sensor, it is possible to accelerate the ionized chemical substances at any time inside the sensor using the first AC electric field. This means that it is possible to increase the transfer distance of ionized compounds and to provide a sensor with even higher separation or selection performance.

It is effective to also include an accumulator that accumulates the substances ejected from the transfer device. The accumulator is capable of selectively accumulating chemical substances confirmed by the detector. It is possible to supply the chemical substances accumulated in the accumulator via a feedback path to the transfer device, have such substances selected once again by the transfer device, raise the detection precision, and have chemical substances with even higher purity accumulated in the accumulator.

Another aspect of the present invention is a synthesizing apparatus (or system) including a plurality of the transfer devices described above. The synthesizing apparatus also includes a reaction chamber that accumulates substances ejected from the plurality of transfer devices and an energy supplying unit supplying reaction energy to the substances inside the reaction chamber. It is possible to select the chemical substances required for synthesis on a molecular level from air or the like using the transfer devices, to feed such substances to the reaction chamber, and to synthesize a desired chemical substance.

It is also effective for the synthesizing apparatus to further include a plurality of accumulators that accumulate substances respectively supplied to the plurality of transfer devices; and a plurality of supplying transfer devices that supply substances to the respective plurality of accumulators. By using the transfer devices, it is possible to select chemical substances used as the sources for synthesis from the atmosphere or the like and to accumulate such substances in advance in the accumulators.

Another aspect of the present invention is a terminal including a detection apparatus and/or a synthesizing apparatus including a transfer device. The transfer device according to the present invention is capable of self-priming, i.e., drawing in the target chemical substances (molecules, atoms) by itself. In addition, it is preferable to realize the transfer device using MEMS or micromachining. Accordingly, in various types of apparatus that use a transfer device, pumps aside from the transfer device may be omitted and the entire apparatus or system can be made extremely compact. This means that it becomes possible to equip a mobile terminal such as a mobile phone or a smartphone with an apparatus or system that uses a transfer device.

Another aspect of the present invention is a method, for example a control method, including transferring substances ionized by a transfer device including a plurality of first electrodes that are aligned in the first direction and a plurality of second electrodes that are aligned in a second direction. Here, the transferring includes steps of:

having the plurality of first electrodes form a first AC electric field for linear driving; and having the plurality of second electrodes form an asymmetric second AC electric field.

Here, the transferring may include transferring the ionized substances toward a detector. Also, the transferring may include transferring the ionized substances toward a reaction chamber.

DETAIL DESCRIPTIONS

Figure 1:
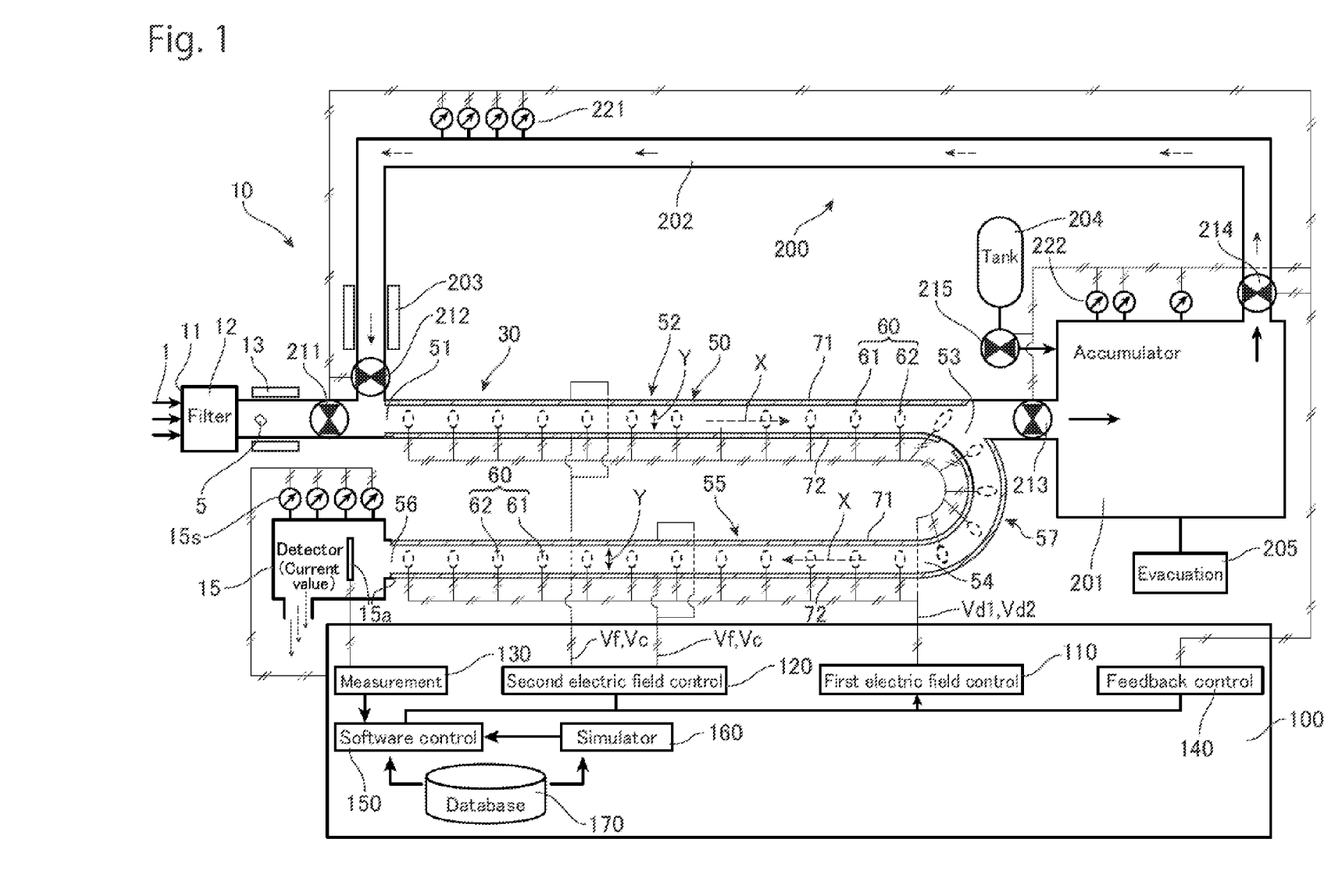
FIG. 1 shows an outline an ion mobility sensor.

FIG. 1 shows an overview of an ion mobility sensor according to the present invention. The sensor 10 includes a suction port 11 for sample gas 1 such as air or breath, a filter 12 that removes foreign matter such as particles included in the drawn-in sample gas 1, an ionizing unit 13 that ionizes constituents included in the sample gas 1 using an appropriate method, a transfer unit (transfer device, ion feeder, ion conveyor) 30 that transfers the ionized substances (chemical substances) using an AC electrical field, and a detector 15 that detects chemical substances conveyed by the transfer unit 30. The transfer unit 30 includes a U-shaped drift tube (feeder) 50, with one straight tube portion 52 whose input side end 51 is connected to the ionizing unit 13 as an inlet tube, the other straight tube portion 55 as a discharge tube, and a one end 56 of the straight tube portion 55 connected to the detector 15. An end 53 of the straight tube portion 52 and an end 54 of the straight tube portion 55 are connected by a bent tube 57.

The ionizing unit 13 may be a type that carries out ionization using a radiation source ($N_{63}$) or a type that carries out ionization using corona discharge. The detector 15 includes a detection electrode 15a which, when ionized chemical substances arrive, measures the amount of chemical substances that have arrived as current values. The detector 15 also includes a sensor group 15s for acquiring environmental conditions, for example, temperature, humidity, pressure, and flow rate, of the detector 15.

The sensor 10 further includes a feedback unit 200 that connects the discharge-side end 53 of the inlet tube 52 of the transfer unit 30 and the input-side end 51. The feedback unit 200 includes an accumulator (separation chamber) 201 that is connected to the discharge-side end 53 of the inlet tube 52 of the transfer unit 30, a bypass tube 202 that connects the accumulator 201 and the input-side end 51 of the transfer unit 30, and an ionizing unit 203 that is provided at the outlet of the connector portion 202 (i.e., at the input side of the transfer unit 30). The feedback unit 200 further includes an inert gas tank (buffer) 204 that controls the internal pressure of the accumulator 201 and an evacuation unit 205 that cleans up the accumulator 201.

In addition, the feedback unit 200 includes valves 211 to 215 for switching between lines and sensor groups 221 and 222 for acquiring environment information for the feedback unit 200.

The drift tube 50 of the transfer unit 30 typically has an overall cylindrical shape with a diameter of 1 μm to 10 mm, preferably 10 μm to 1000 μm, and even more preferably 10 μm to 500 μm. The drift tube 50 includes two half-cylindrical electrode plates ("second electrodes" or "semi-cylindrical electrodes") 71 and 72. Such electrode plates 71 and 72 are assembled with insulators in between so as to construct the outer wall of the tube 50. The electrode plates 71 and 72 are separated into a group that constructs the inlet tube 52 and a group that constructs the bent tube 57 and the discharge tube 55, so that separate electric fields can be formed by the respective groups. Note that in situations where the applied voltage can be increased, the diameter of the drift tube 50 can be increased further. Also, the drift tube 50 may have a rectangular cross-section and for example be a square or rectangular tube.

The drift tube 50 also includes a plurality of ring-shaped electrodes (first electrodes) 60 disposed in an axial direction X of the drift tube 50 in a vicinity of the center of the electrode plates 71 and 72. The ring-shaped electrodes 60 are disposed at appropriate intervals, with voltages with respectively different polarities being applied to adjacent electrodes, for example, the odd-numbered electrodes 61 and the even-numbered electrodes 62. The intervals between the electrodes 60 may be 1 μm to 1000 μm, for example, and preferably 10 μm to 500 μm. The diameter of the ring-shaped electrodes 60 is 1 μm to 1000 μm, preferably 10 μm to 500 μm, and even more preferably 10 μm to 100 μm. Note that in situations where the applied voltage can be increased, the sizes of the respective ring-shaped electrodes may be increased. The plurality of ring-shaped electrodes 60 are separated into a group that forms an electric field inside the inlet tube 52 and a group that forms an electric field inside the bent tube 57 and the discharge tube 55, with it being possible to form separate electric fields using the respective groups.

The sensor 10 includes a driving control unit 100 that supplies power to the ring-shaped electrodes 60 and the electrode plates 71 and 72 and controls the electric fields formed by such electrodes. The driving control unit 100 (or "control unit") 100 includes a first electric field control unit 110 that has a first AC electric field for linear driving formed by the ring-shaped electrodes 60 and a second electric field control unit 120 that has an asymmetric second AC electric field formed by the electrode plates 71 and 72.

The first electric field control unit 110 regularly switches the polarities of the voltages Vd1 and Vd2 applied to the odd-numbered electrodes 61 and the even-numbered electrodes 62 out of the ring-shaped electrodes 60 to regularly reverse the directions of the electric fields formed by the adjacent electrodes 61 and 62. By doing so, a first AC electric field for linear driving that causes the ionized chemical substances (ionized target chemicals, hereinafter "ions" or "ionized molecules") included in the sample gas 1 to travel in the axial direction (or "X direction) is formed by the ring-shaped electrodes 60. The voltages Vd1 and Vd2 are AC voltages or pulse-type switched voltages of around 0.1 to 50 MHz and around 10 to 200V. The frequencies and voltages of the voltages Vd1 and Vd2 depend on the sizes and intervals of the ring-shaped electrodes 60 and do not need to be in the ranges given above.

The second electric field control unit 120 applies an AC voltage (AC electric field) Vf and a compensation voltage Vc to the electrode plates 71 and 72 to form an asymmetric AC electric field in the Y direction (second direction) that is perpendicular to the axial direction X. The AC voltage Vf is a high-frequency wave of around 0.1 to 50 MHz and around 10 to 200V and the compensation voltage Vc is a DC voltage suited to forming an asymmetric electric field within the range of the AC voltage. The AC voltage Vf and the DC voltage Vc depend on the sizes and the gaps between the electrode plates 71 and 72 and do not need to be in the ranges given above.

The driving control unit 100 also includes a measurement unit 130 that acquires the amount of a target chemical substance 5 discharged to the detector 15 by the transfer unit 30 as a current value, a feedback control unit 140 that monitors and controls the feedback unit 200, a software control unit 150 that uses software to change the set values of the electric field control units 110 and 120 based on measurement values obtained from the detector 15, a simulator 160, and a database 170. The measurement unit 130 acquires environmental information from the sensor group 15s of the detector 15 in addition to the current values that are measurement values, and corrects the measurement values. The feedback control unit 140 controls the valves 211 to 215 provided in the feedback unit 200 to carry out line switching, and also acquires values of the sensor groups 221 and 222 and monitors the states and the like of the various parts of the feedback unit 200, such as the accumulator 201.

Figure 2:
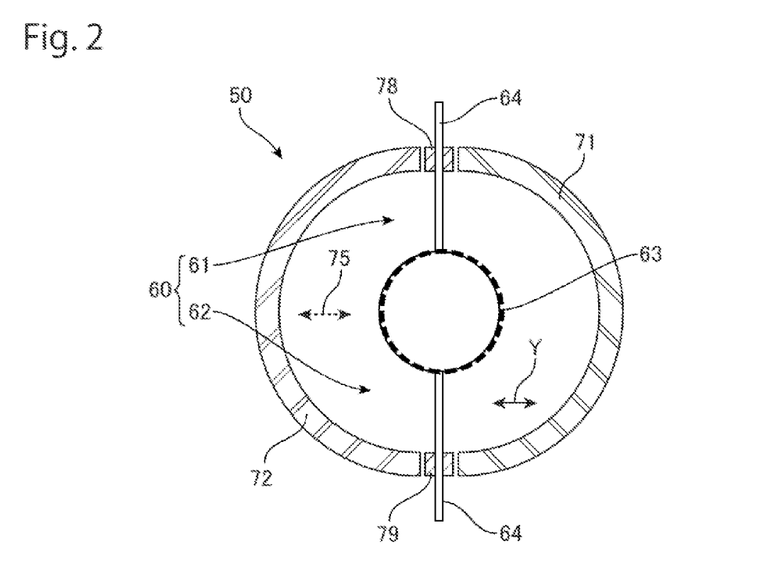
FIG. 2 is a cross-sectional view showing an outline of a drift tube.
Figure 3:
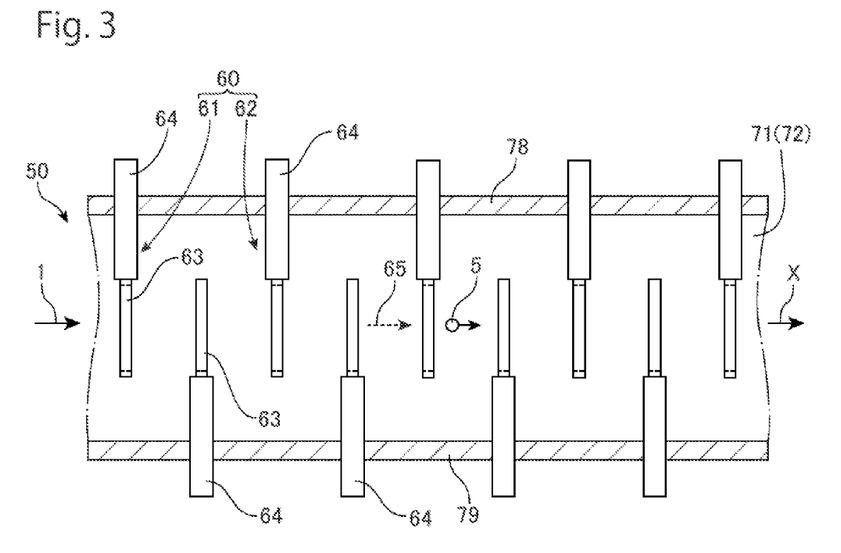
FIG. 3 is a cross-sectional view in another direction showing outline of the drift tube.

FIG. 2 is a cross-sectional view for a case where the drift tube 50 has been cut along the direction Y that is perpendicular to the inflow direction of the sample gas 1, that is, the axial direction X. FIG. 3 is a cross-sectional view for a case where the drift tube 50 has been cut along the inflow direction of the sample gas 1, that is, the axial direction X. The tube 50 has a cylindrical outer wall constructed by assembling the two semi-cylindrical (or half-cylindrical) electrode plates 71 and 72 with insulators 78 and 79 in between.

Ring-shaped microelectrodes 61 and 62 are disposed at appropriate intervals along the axial direction X in the vicinity of the center of the drift tube 50. The respective electrodes 61 and 62 each include a ring-shaped tip portion 63 and a lead 64 that passes through the insulators 78 and 79 and appears on the outside of the drift tube 50 so as to supply power to the tip portion 63. In the construction in FIG. 2 and FIG. 3, the leads 64 of the odd-numbered electrodes 61 and the leads 64 of the even-numbered electrodes 62 extend in different directions, which facilitates the application of voltages Vd1 and Vd2 of different polarities to the leads 64. However, the arrangement of the leads 64 of the electrodes 61 and 62 is not limited to this.

Figure 4:
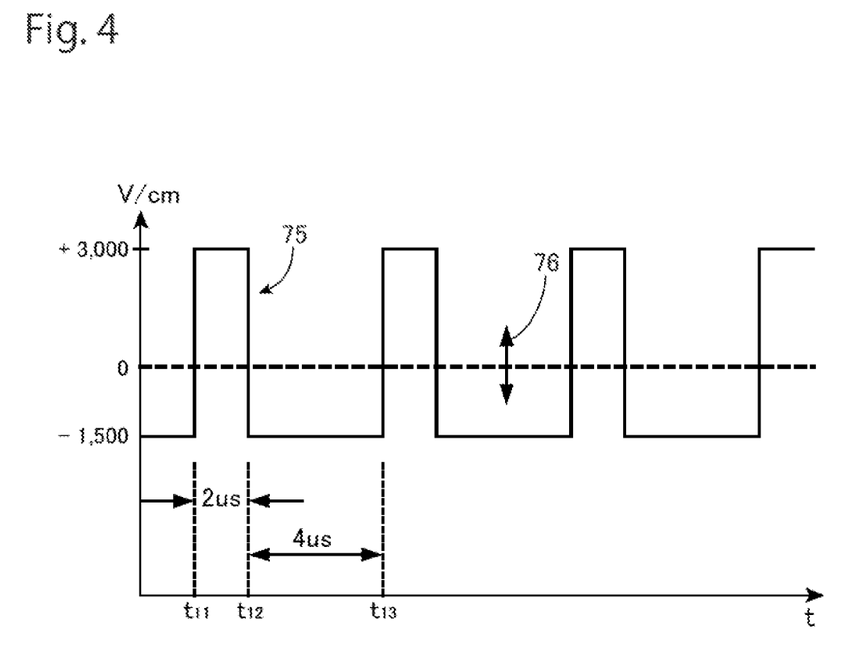
FIG. 4 is a diagram showing changes in the voltage that forms an asymmetric AC electric field.

FIG. 4 shows one example of an asymmetric AC voltage applied to the electrode plates 71 and 72. By combining the AC voltage (AC electric field) Vf and the DC compensation voltage Vc, an asymmetric electric field 75 that changes in a pulse-like manner at time t11, t12, and t13 is formed. By changing the compensation voltage Vc to change the asymmetry of the asymmetric electric field 75 as shown by the arrow 76, it is possible to control the displacement (deflection) in the Y direction of ions 5 that pass through the drift tube 50.

Figure 5:
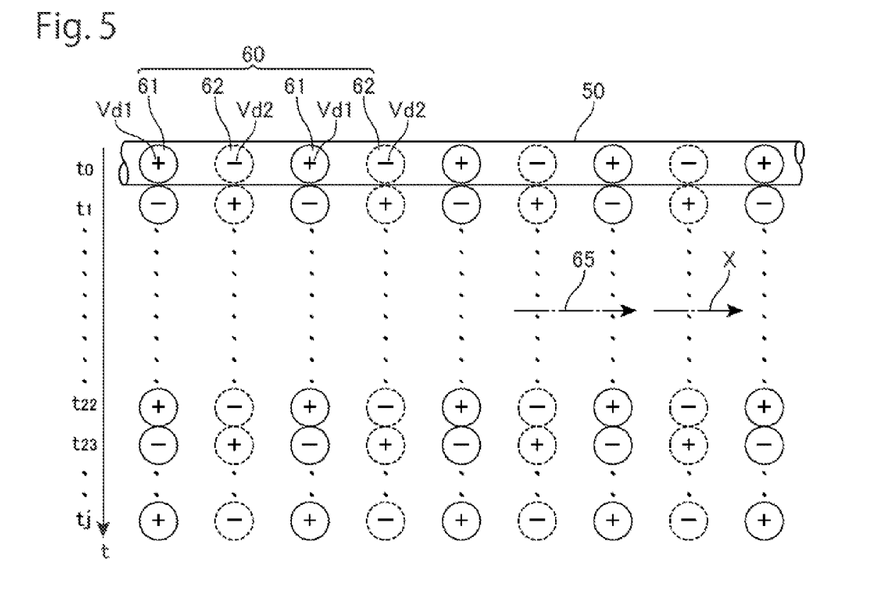
FIG. 5 is a diagram showing variation in an AC electric field for linear driving.

FIG. 5 shows how the voltages (driving voltages) Vd1 and Vd2 with different polarities are applied via the ring-shaped microelectrodes 61 and 62. As shown in FIG. 5, the voltages Vd1 and Vd2 respectively applied to the microelectrodes 61 and 62 of the drift tube 50 are switched so that the polarities thereof alternately differ at intervals of a predetermined time, i.e., when the elapsed time reaches the times t0, t1 to t22, and t23. As a result, a first AC electric field 65 for linear driving is formed in the axial direction X.

Figure 6:
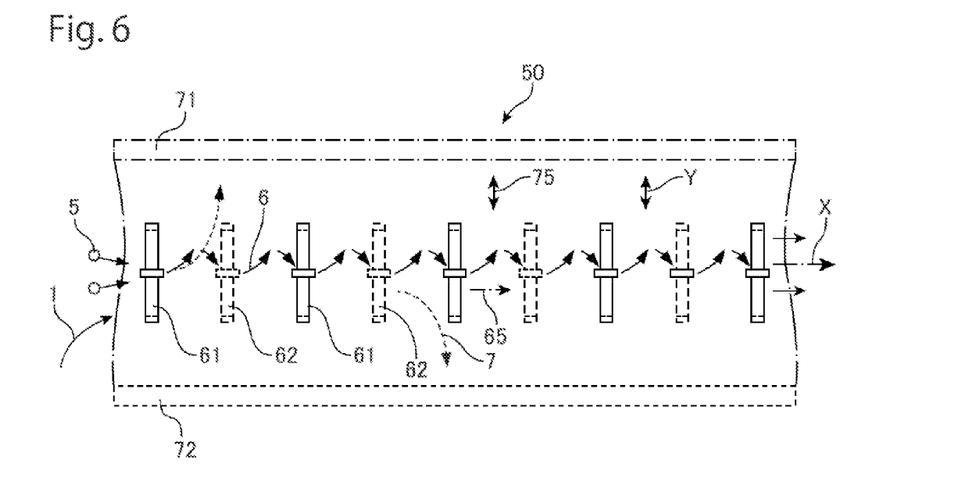
FIG. 6 is a diagram showing how ions move in the drift tube.

FIG. 6 schematically shows how ionized molecules 5 move inside the drift tube 50. If the frequency f1 and electric field strength E1 of the first AC electric field 65 for driving formed by the driving voltages Vd1 and Vd2 supplied to the microelectrodes 61 and 62 are in a matching (synchronized) relationship with the mobility K of the target molecules 5, as shown by the arrow 6 drawn with a solid line, the synchronized molecules 5 will accelerate in the axial direction X of the drift tube 50 due to the principles of a linear motor. The ions 5 that have passed the drift tube 50 reach the detection electrode 15a of the detector 15 that is provided at the outlet 56 of the drift tube 50 and are detected as an ion current.

On the other hand, as shown by the arrow 7 drawn with a broken line, molecules where the mobility K does not match (i.e., is not synchronized with) the frequency of the AC electric field 65 for driving formed by the microelectrodes 61 and 62 are deflected toward the electrode plate 71 or 72, contact such electrode plate 71 or 72, and are discharged. Accordingly, such molecules are not detected as an ion current. That is, since the charge is lost when ionized molecules 5 collide with the electrode plate 71 or 72, the detector 15 will not measure a current value for such substance and such molecules will not be detected by the detector 15 even if they pass through the drift tube 50. This is also the case when ionized molecules contact the microelectrodes 61 or 62.

That is, the ring-shaped microelectrodes 61 and 62 are disposed along the center axis X of the drift tube 50 constructed by the electrode plates 71 and 72, are positioned midway between the electrode plates 71 and 72, and are disposed inside the asymmetric second AC electric field 75 that is formed by the electrode plates 71 and 72. Accordingly, the ionized molecules 5 drawn into the drift tube 50 are influenced by the first AC electric field 65 for linear driving and are also influenced by the asymmetric second electric field 75 that is formed in the Y direction by the electrode plates 71 and 72. For this reason, the molecules 5 that do not move inside the tube 50 under the first AC electric field 65 for linear driving are influenced by the second AC electric field 75, are excluded from the range of the ring-shaped microelectrodes 61 and 62, and lose their charge.

With FAIMS technology that filters ionized chemical substances using an asymmetric electric field, it is known that molecules (target chemical substances) 5 for which there is a matching relationship between the asymmetric AC electric field 75 formed by the AC voltage Vf and the compensation voltage Vc and the ion mobility K will be concentrated in the vicinity of the center of the electrode plates 71 and 72. Accordingly, by synchronizing the first AC electric field 65 for linear driving formed by the ring-shaped electrodes 61 and 62 disposed in the vicinity of the center of the electrode plates 71 and 72 with the ion mobility K of the molecules 5 gathered by the asymmetric second AC electric field 75, it is possible to convey the molecules 5 filtered by the asymmetric second AC electric field 75 in a predetermined direction X using the drift tube 50. For this reason, it is possible to directly feed the target chemical substances 5 via the drift tube 50 in a desired direction, for example toward the detector 15 without depending on a carrier gas.

Figure 7:
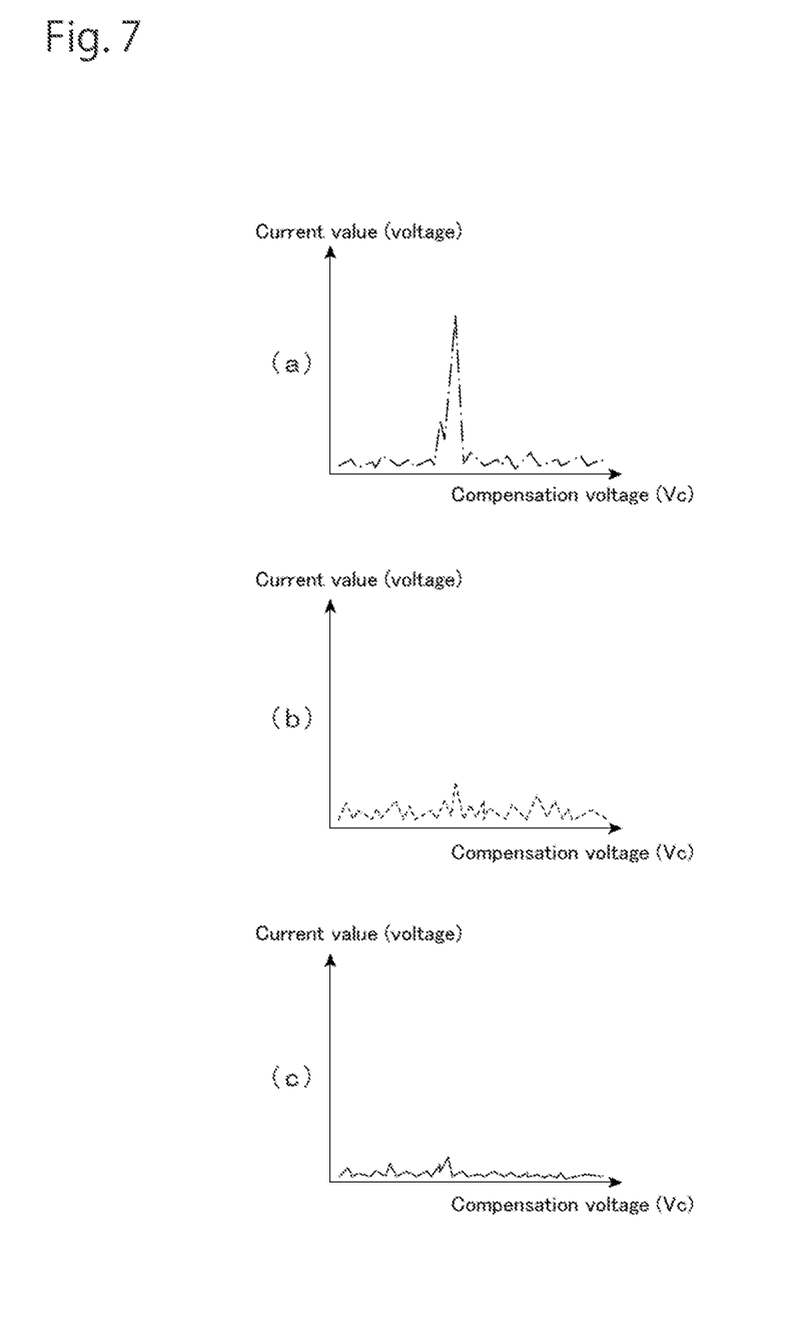
FIG. 7 is a series of diagrams showing how an ion current changes according to changes in a field switching rate, with FIG. 7(a) showing changes in a current value obtained by a first switching rate, FIG. 7(b) showing the same for a second switching rate, and FIG. 7(c) showing the same for a third switching rate.

FIGS. 7(a) to 7(c) show a number of examples of the frequency (field switching rate) of the voltages Vd1 and Vd2 that form the first AC electric field 65 for linear driving and the ion currents detected for such frequencies. By changing the field switching rate, the ions 5 conveyed by the drift tube 50 of the transfer unit 30 will change, resulting in a change in the ions 5 fed to the sensor 15. Accordingly, the ions 5 that pass the sensor change and the values (spectra) of the ion currents also change.

With the transfer unit 30, it is possible, using the driving control unit 100, to control one or both of the conditions of the first AC electric field 65 for linear driving and the conditions of the asymmetric second AC electric field 75 via software. In particular, by controlling the conditions of the first AC electric field 65 for linear driving using software, it is possible to control the flow rate of molecules (sample gas) flowing in the drift tube 50 of the transfer unit 30. This means that compared to when the flow rate of the carrier gas is controlled mechanically, it is possible to control the flow rate (flow speed) of gas inside the drift tube 50 more precisely. Accordingly, in the sensor 10 equipped with the transfer unit 30, by controlling the drift velocity of the ions 5 more precisely, it is possible to measure stably and with high precision.

For example, using the value of the AC voltage Vf and the value of the compensation voltage Vc that form the electric field 75, it is fundamentally possible to selectively measure ionized chemical substances that are to be measured. In addition, by generating the first AC electric field 65 for linear driving so as to match the ionized chemical substances to be measured, it is possible to improve the selectivity (filtering performance) of the transfer unit 30. Accordingly, the detection current values (waveforms) of the detector 15 that detects the ions 5 fed in by the transfer unit 30 are expected to be clear and highly precise. Regarding the switching rate of the first AC electric field 65 for linear driving, by using the software control unit 150, it is also possible to adjust and discover a combination with higher sensitivity with the current values (measurement values) detected by the detector 15 as a target. Accordingly, with the sensor 10, by carrying out software control, a condition (switching rate) of the first AC electric field 65 for detecting the target ions 5 is changed within a wide switching range and a condition with more favorable detection efficiency is found from the detection voltage values (peak waveforms) obtained as a result. After this, conditions where the target ions are detected by the sensor 10 are finally decided as a sweet spot.

Figure 8:
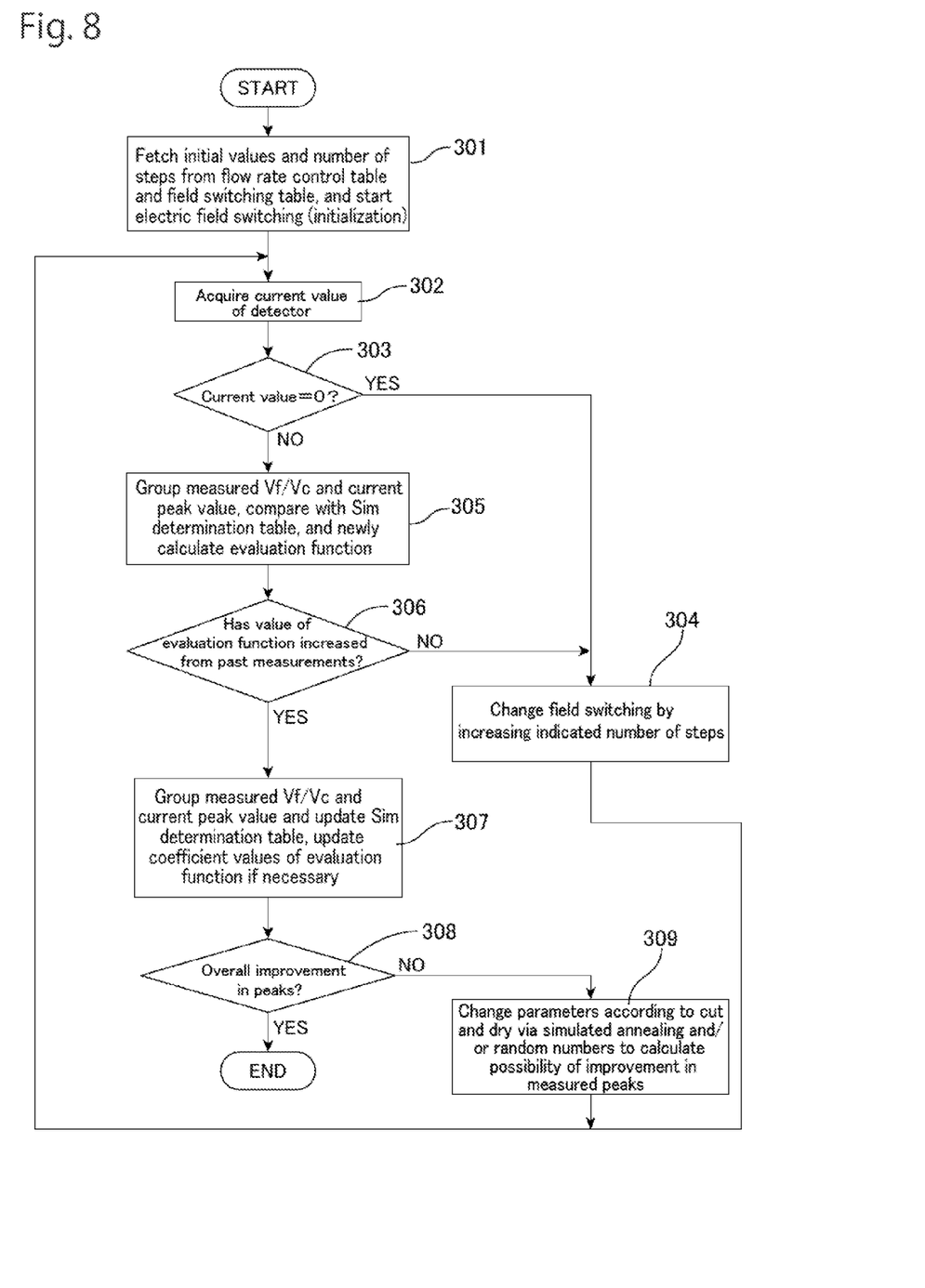
FIG. 8 is a flowchart showing an example of processing by a software control unit.

FIG. 8 shows one example of processing by the software control unit 150. In step 301, the initial values and number of steps are fetched from a flow rate control table and an field switching conversion table provided in the database 170, and field switching is started (initialization). By doing so, the first AC electric field 65 for linear driving is formed inside the drift tube 50 by the transfer unit 30 by the ring-shaped electrodes 61 and 62.

In step 302, the current values of the detector 15 are acquired by the measurement unit 130. The current values show the amount of ionized chemical substances fed into the detector 15 by the transfer unit 30. If, in step 303, the current value is zero, in step 304 the indicated number of steps is increased, the field switching is changed, and the conditions of the first AC electric field 65 for linear driving are changed.

If the current value is not zero, in step 305, the conditions, that is, the AC voltage Vf and the compensation voltage Vc, forming the asymmetric second electric field 75 of the drift tube 50 of the transfer unit 30 during the current measurement are grouped with the current peak values obtained from the detector 15 and correlated. Profiles of respective chemical substances, for example, the correlation between the AC voltage Vf and the compensation voltage Vc and peaks in a standard state provided in the database 170 are simulated using the simulator 160 so as to match the present measurement conditions, and a simulation determination table is generated. The acquired correlation and the simulation determination table are then compared to newly calculate an evaluation function.

In step 306, if the value of the evaluation function has not increased from past measurements, in step 304 the conditions of the first AC electric field 65 for linear driving are changed.

On the other hand, if in step 306 the value of the evaluation function has increased from past measurements, in step 307 the correlation between the conditions Vf and Vc of the second current field measured this time and the current peak values are further considered and the simulation determination table is updated. If necessary, the coefficient values of the evaluation function are updated.

If, in step 308, improvement in the peaks for all current values obtained by the detector 15 are observed, the conditions of the first AC electric field 65 and the second AC electric field 75 formed in the drift tube 50 of the transfer unit 30 are maintained and measurement by the sensor 10 continues. If improvement is not observed, in step 309 parameters are changed according to cut and try via simulated annealing and/or random numbers and the possibility of improvement in the measured peaks is calculated.

In the sensor 10 that uses the transfer unit 30, desired ions 5 are filtered and autonomously conveyed by the transfer unit 30 to feed the ions 5 into the detector 15. Accordingly, it is possible to directly feed the target chemical substances to the detector without relying on carrier gas. In the drift tube 50 of the transfer unit 30, there is a tendency for the target chemical substances to be concentrated by the first AC electric field 65 and the second AC electric field 75, resulting in the possibility of the partial pressure inside the drift tube 50 rising and/or the concentration increasing so that the molecules violently collide with each other. Accordingly, it is preferable for the concentration of the target chemical substances included in the introduced sample gas 1 to be a quite a low level. On the other hand, since a high flow rate is not required as with a conventional carrier gas, it is not necessary to forcibly raise the concentration of the sample gas 1. This means that it is possible to provide a high-precision sensor 10 that is capable of detecting even chemical substances of a low concentration.

Another advantage of the sensor 10 that uses the transfer unit 30 according to this technology is that although the measurable range of current values with FAIMS is exceeded when the concentration of the ionized chemical substances to be measured exceeds a certain level, by using the transfer unit 30 to limit the amount of chemical substances that reach the detector 15, it can be possible to keep the concentration within the measurable range. That is, it is possible to realize automatic measurement that monitors the current values of the detector 15 and automatically amends the transfer speed of the transfer unit 30 to electronically carry out flow rate control. For chemical substances where the FAIMS characteristics (that is, the conditions of the second AC electric field 75) have been established in a database for which characterization is complete, it is possible to realize automatic measurement by controlling the conditions of the second AC electric field 75 and the conditions of the first AC electric field 65 formed in the transfer unit 30 in accordance with the concentration of the measured chemical substances included in the sample gas 1 so as to change the flow rate of the sample that reaches the detector 15.

In this sensor 10, the transfer unit 30 selectively draws and feeds the target chemical substances. Accordingly, there is reduced probability that substances aside from the target chemical substances with be drawn in by the transfer unit 30 and it is also possible to omit a carrier gas that includes dust and the like and is forcibly fed to the sensor. For this reason, although a FAIMS analysis apparatus is normally equipped with carbon fibers and/or a microfilter in front of the input into the apparatus, it is possible here to omit such filters. Although such filters normally use a technology that removes dangerous particles that can affect measurement, from the viewpoint of the entire system, such filters cause a drop in pressure, making an even larger amount of high-pressure carrier gas necessary to maintain the pressure. This means it is necessary to provide a large number of filters and to increase the number of pumps to maintain a constant pressure balance, thereby causing an increase in cost.

Figure 9:
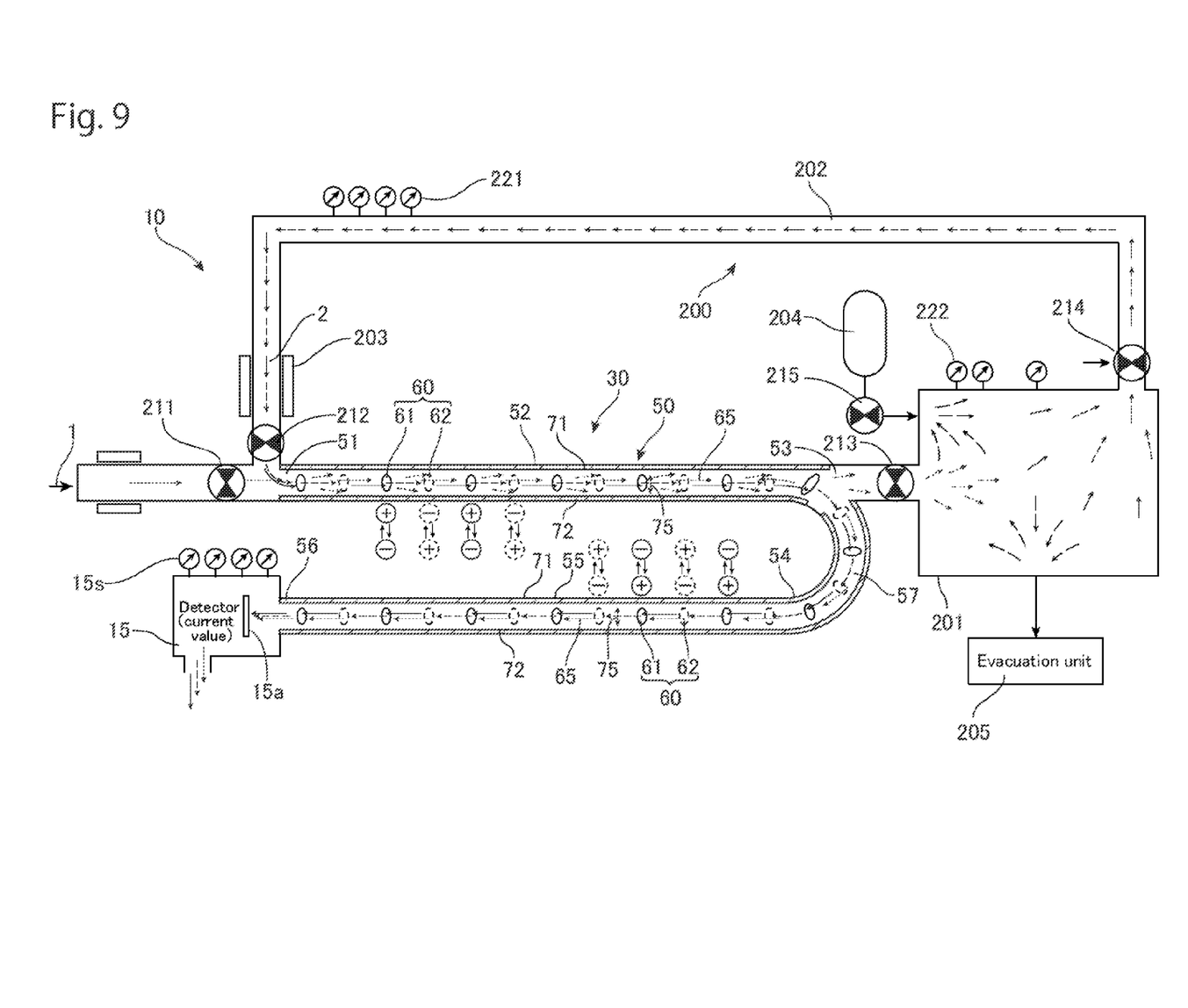
FIG. 9 shows a usage state of a feedback unit.

FIG. 9 shows one example of processing that measures chemical substances using the sensor 10 equipped with the transfer unit 30 and the feedback unit 200. First, the feedback control unit 140 opens the first control valve 211 provided on the input side 51 of the drift tube 50 to input the sample gas 1. As described earlier, since the transfer unit 30 is equipped with a function as an ion conveyor, the sample gas 1 can be acquired even if a mechanical pump or carrier gas is not used. That is, the ion sensor 10 is capable of autonomously drawing in the sample gas 1 from the atmosphere.

When a predetermined amount of gas has been drawn in, the first control valve 211 is closed and is not opened until measurement ends. At the same time as the first control valve 211 opens, a fifth control valve 215 for introducing the inert gas 204 into the accumulator 201 is closed, the fourth control valve 214 that connects the accumulator 201 and the bypass tube 202 is also closed, and a third control valve 213 that connects the discharge end of the inlet tube 52 of the drift tube 50 and the accumulator 201 is opened.

The accumulator (separation chamber) 201 is placed in advance in an evacuated state by the evacuation unit 205 and at such stage the accumulator 201 is shut off from the evacuation unit 205. In this state, once the first AC electric field 65 for linear driving has been formed by the first electrodes 60 (61 and 62) of the drift tube 50 and the asymmetric second AC electric field 75 has been formed by the second electrodes 71 and 72, the chemical substances 5 to be measured are separated from the sample gas 1 by the inlet tube 52 of the drift tube 50 and fed to the accumulator 201.

Once the internal pressure of the accumulator 201 has reached one atmosphere like the outside atmospheric pressure, the third control valve 213 is closed to separate the accumulator 201 from the drift tube 50, and the drift tube 50 is purged (placed in a state of equilibrium). As one example, the first AC electric field 65 for linear driving and the asymmetric second AC electric field 75 are driven according to various conditions so that the concentration balance of the substances present inside the drift tube 50 is placed in a state of equilibrium. After this, the first control valve 211 that connects the input side of the drift tube to the atmosphere is closed.

After this, the second control valve 212 that connects the bypass tube (feedback loop) 202 and the input side 51 of the drift tube 50, the fifth control valve 215 that introduces the inert gas 204 into the accumulator 201, and the fourth control valve 214 that connects the accumulator 201 and the bypass tube 202 are opened. By carrying out this operation, the gas accumulated in the accumulator 201 is fed back via the ionizing unit 203 to the drift tube 50. The constituents included in the gas accumulated in the accumulator 201 are mainly constituents that have been filtered by the drift tube 50 and are a gas (concentrated gas) 2 with a high concentration of the chemical substances 5 to be measured.

If the concentration of the gas (concentrated gas) 2 accumulated in the accumulator 201 is to be raised further using the inlet tube 52 of the drift tube 50, the second control valve 212 is opened and the third control valve 213 is also opened so that the discharge side 53 of the inlet tube 51 of the drift tube 50 is connected to the accumulator 201. The fifth control valve 215 gradually introduces the inert gas 204 into the accumulator 201 while carrying out switching control so that the internal pressure of the accumulator 201 is the same as the outside atmospheric pressure. By doing so, although gas is forcibly supplied from the accumulator 201 to the bypass tube 202 while maintaining a constant pressure, such supplying is carried out gradually. Such supplying only needs to maintain an appropriate return (feedback) flow rate while avoiding an extreme drop in the internal pressure in the accumulator 201.

If a substance to be measured included in the sample gas 1 has an extremely low concentration, by using the feedback unit 200 to feed back to the drift tube 50 multiple times, it is possible to raise the concentration of the chemical substances to be measured inside the accumulator 201. As one example, the accumulator 201 may be a compressing chamber including an adsorption material such as porous glass, and can be realized by an extremely small container. The concentration adjustment can store a number of feedback iterations that use the feedback unit 200. Also, by raising the temperature of the porous glass or the like, it is possible to release the chemical substances adsorbed by the accumulator 201 at the same time to raise the concentration.

When detecting the types and concentrations of the chemical substances to be measured that are included in the concentrated gas 2 in the accumulator 201 using the detector 15, the second control valve 212 that connects the drift tube 50 and the bypass tube 202 is opened and the third control valve 213 that connects the drift tube 50 and the accumulator 201 is closed. The concentrated gas 2 is conveyed by the inlet tube 52, the bent tube 57, and the discharge tube 55 of the drift tube 50 and is discharged to the detector 15 attached to the discharge side 56 of the discharge tube 55. After this, the ionized molecules included in the discharged gas are measured as current values.

In this way, the ion sensor 10 including the transfer unit 30 can omit a mechanical pump for causing the sample gas 1 to flow to the sensor 10. That is, in the sensor 10, the sample gas 1 may be drawn or supplied using a pump, but it is not necessary to use a pump.

With a conventional FAIMS sensor that separates ions using an asymmetric electric field, after the ionizing unit is passed, an asymmetric voltage is applied to the two electrode plates at the same time as the flight path is formed, and a gas flow with a constant flow amount (flow rate) and a constant pressure is generated by a mechanical pump to cause the sample gas to flow toward the detector. On the other hand, with the transfer unit 30 used in the sensor 10 according to the present embodiment, in addition to a system that forms an asymmetric AC electric field, microelectrodes that are produced by micromachining and have the polarities of adjacent electrodes switched alternately between plus and minus are provided so that ions are linearly driven inside the drift tube 50. Accordingly, the ionized chemical substances move so as to be pushed in the direction of the detector.

With the sensor 10 and a sensor system that uses the sensor 10, unlike a conventional FAIMS type sensor, switching control for moving (conveying) the target chemical substances is carried out in accordance with or corresponding to the molecular weight, ion mobility, and ionization amount of the chemical substances. Since ion mobility is also related to such mechanism, in addition to the conveying of the target chemical substances, a filtering effect is simultaneously obtained. Accordingly, even if the target chemical substances are present in the atmosphere in an extremely low concentration, it is still possible to convey such substances as a target to the detector 15 and have such substances reliably detected even in a low concentration.

In addition, the sensor 10 uses the transfer unit 30 to collect and concentrate the target chemical substances in the accumulator 201. Accordingly, it is possible to detect the target chemical substances with even higher sensitivity.

By also providing the feedback unit 200 and separating multiple times and measuring multiple times using the feedback loop (bypass tube) 202, it is possible to measure substances outside the measurement range due to measurements of ionized chemical substances being hidden by differences in the energy of proton affinity and/or electron affinity.

That is when measuring ions using FAIMS technology, there are cases where indirect ionization is used by the ionizing unit, and in such cases, due to proton affinity and/or electron affinity, there are cases where the ratio of ion exchange (transfer) changes according to the combination of chemical substances included in the sample to be measured or the carrier gas, resulting in a change in the measurement data that makes measurement difficult. In cases where samples are analyzed and specified using indirection ionization via a radiation source, corona discharge, or the like, the ease of ionization will change according to the target chemical substances and combinations thereof. For this reason, in some cases it has been extremely difficult to measure the target chemical substances as absolute values (i.e., as merely current values). That is, there have been cases where depending on the measured sample, in fortunate circumstances clear and highly reliable measurement was possible, but depending on the combination, measurement was difficult unless indirect ionization is carried out using UV (ultraviolet).

In this sensor 10, not only is high concentration gas 2 formed in the feedback unit 200, ionization also occurs in the ionizing unit 203 every time the bypass tube 202 is passed. Accordingly, it is possible to stabilize the state (ionized state) of the gas that reaches the detector 15 and to stably carry out measurement.

Also, in the ion sensor 10, the transfer unit 30 feeds the ionized chemical substances into the accumulator 201 using the drift tube 50 that functions like an electric field differential pump, and it is possible to supply substances to the detector 15 starting with those for which proton affinity or electron affinity ionization is easy and to successively measure and exhaust the measured substances. By doing so, it becomes possible to measure even chemical substances with low ionization "priority" by passing through the feedback loop 202 and measuring multiple times.

In addition, by switching the characteristics of the drift tube 50 (i.e., the characteristics of the first AC electric field for linear driving) between characteristics for conveying plus ions and characteristics for conveying minus ions, it is possible to concentrate, detect, and exhaust plus and minus ions according to separate conditions. In this way, since it is possible for the drift tube 50 to select and convey ions according to various conditions, by increasing the number of times the drift tube 50 is passed, it is possible to selectively increase the purity of the chemical substances to be measured and to acquire measurement results with higher precision.

Figure 10:
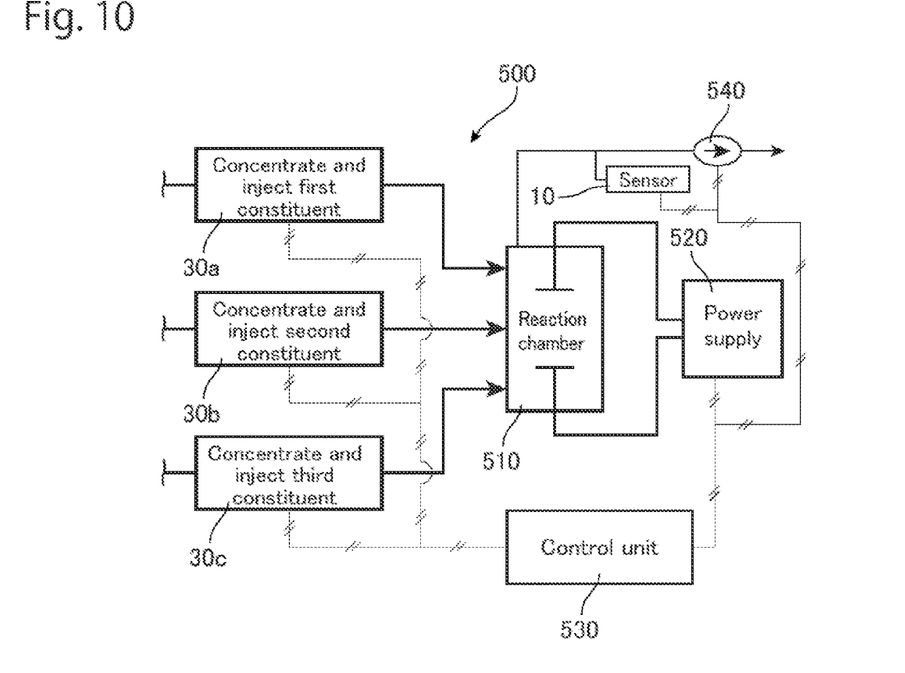
FIG. 10 shows an outline of the synthesizing apparatus.

FIG. 10 shows an overview of a synthesizing apparatus 500 for chemical substances according to software control on a Nano-level. The synthesizing apparatus 500 includes three transfer units (or "transfer devices", "ion pumps", "ion feeders", "ion conveyors", "ion injectors") 30a, 30b, 30c, a chemical reaction chamber 510 into which chemical substances are injected by such transfer devices (transfer apparatuses), a power supplying unit (energy supplying unit) 520 that applies an electric field to the chemical reaction chamber 510, a reaction control unit 530 for switching control of chemical reactions by switching the electric field on and off, a pump 540 that discharges the synthesized product, and the ion mobility sensor 10 for confirming the constituents of the synthesized product. The three transfer units 30*a*, 30*b*, and 30*c* have a function for concentrating different constituents of the atmosphere (a first constituent, a second constituent, and a third constituent) in their respective accumulators and injecting the respective constituents into the chemical reaction chamber 510.

Figure 11:
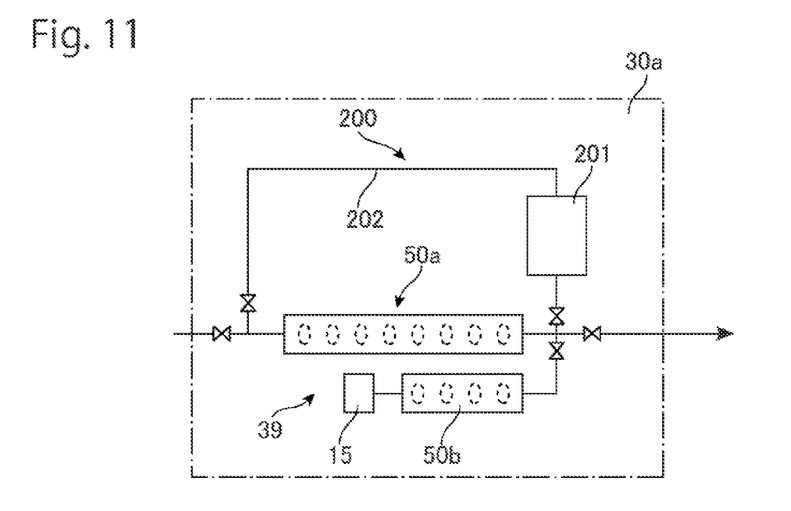
FIG. 11 shows an outline of a transfer unit.

FIG. 11 shows an outline of the transfer unit 30*a*. The other transfer units 30*b* and 30*c* have the same construction. The transfer unit (transfer device) 30*a* includes a first drift tube 50*a* and the feedback unit 200, with it being possible using the first drift tube 50*a* to select a predetermined constituent from the atmosphere and convey and store such constituent in the accumulator 201. The transfer unit 30*a* further includes a second drift tube 50*b* and the detector 15 which construct an ion mobility sensor 39. Accordingly, it is possible to monitor the constituent stored in the accumulator 201 using the ion mobility sensor 39 built into the unit and also possible to monitor constituents injected (ejected) into the chemical reaction chamber 510.

In the transfer unit 30*a*, the drift tube 50*a* that collects the predetermined constituent from the atmosphere in the accumulator 201 also functions as a drift tube that supplies predetermined constituents from the accumulator 201 to the chemical reaction chamber 510, it is also possible to separately provide a drift tube used for collection and a drift tube used for supplying. Since the collecting and supplying of a predetermined constituent can be carried out in parallel, it is possible to suppress depletion of the source (resource) used in synthesis.

By controlling the conditions of the first AC electric field and the second AC electric field of the drift tube 50*a*, the respective transfer units 30*a* to 30*c* are capable of selecting molecules in the atmosphere with extremely high precision and accumulating such molecules in the accumulator 201. In addition, by controlling the conditions of the first AC electric field and the second AC electric field of the drift tube 50*a*, it is possible to convey an extremely small amount of chemical substances and possible to control the amount of chemical substances at a level that is close to molecule units. Accordingly, it is possible to provide an almost maintenance-free synthesizing apparatus 500 that is capable of synthesizing an extremely small amount of chemical substances using the chemical reaction chamber 510 and also collecting resources for synthesis from the atmosphere.

To select or find an appropriate enzyme or catalyst to promote the chemical reaction, large amounts of time and effort were conventionally necessary. With the synthesizing apparatus 500, it is possible to select the required chemical substances with higher precision and guide such chemical substances to the chemical reaction chamber 510, and by controlling the amounts and types of the chemical substances, it is possible to synthesize a variety of substances continuously or instantaneously in the chemical reaction chamber 510. In the chemical reaction chamber 510, aside from electrical power, it is possible to provide energy for synthesis using light, a magnetic field, or the like, and to also dispose an appropriate catalyst inside the chemical reaction chamber 510. If synthesis is not time constrained, it is possible to have the chemical reaction carried out by a catalyst or an enzyme, and possible to use a testing apparatus that selects a catalyst or an enzyme that causes the desired reaction.

Also, the constituents generated or synthesized by the chemical reaction chamber 510 can be fed back as resources for the next synthesis. The synthesizing apparatus 500 can be constructed so that a product of the chemical reaction chamber 510 is selected by the transfer unit 30 in which appropriate conditions are set, is accumulated in the accumulator 201, and is supplied to the chemical reaction chamber 510 at different timing. As one example, oxygen, nitrogen, and carbon dioxide in air are selected as original sources of an organic product, lower organic substances with a low carbon number are first synthesized in the chemical reaction chamber 510, and then such substances are used as resources to synthesize a higher organic substance with a high carbon number. The synthesizing apparatus 500 can be applied in a variety of fields. One example is an odor generating apparatus.

Figure 12:
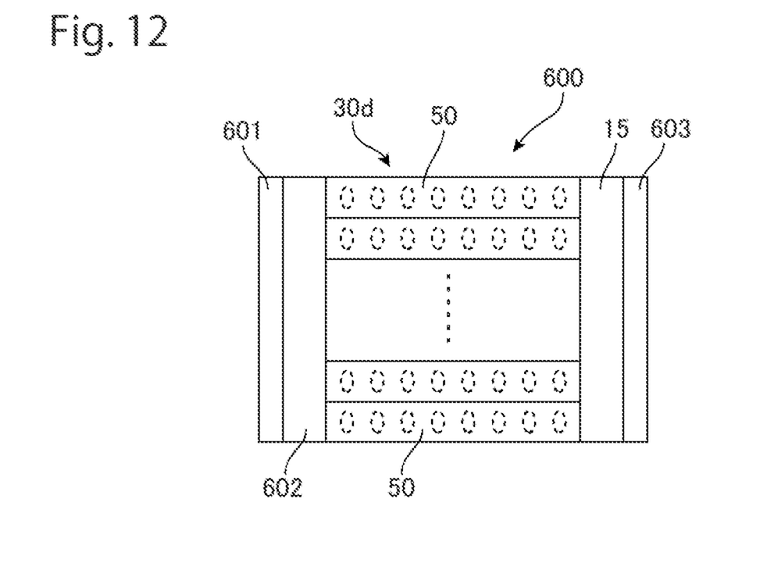
FIG. 12 shows another example of an ion mobility sensor.

FIG. 12 shows a different example of an ion mobility sensor including a transfer unit (transfer device). This sensor 600 includes an input port 601, an ionizing unit 602, a transfer unit 30*d*, the detector 15, and an exhaust port 603. The transfer unit 30*d* includes a plurality of drift tubes 50 disposed in parallel. By disposing the plurality of drift tubes 50 in parallel, it is possible to increase the amount of sample gas that can be drawn in. A favorable size for one drift tube 50 is around several μm to several hundred μm. Accordingly, even if a plurality of drift tubes 50 are disposed in parallel, the size of the entire ion mobility sensor 600 will be several mm to several cm, and since the transfer unit 30*d* does not need a mechanical pump, it is possible to provide an ion mobility sensor that has an extremely simple construction, is compact, and is capable of being easily built into a mobile terminal such as a mobile phone.

Figure 13:
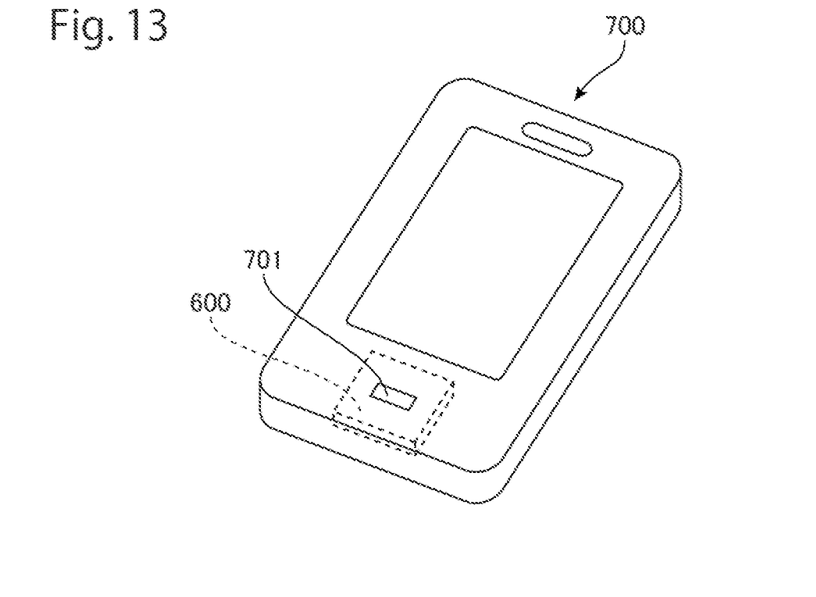
FIG. 13 shows a mobile terminal equipped with an ion mobility sensor.

FIG. 13 shows an example where the ion mobility sensor 600 and a microphone 701 are built into a mobile telephone terminal 700. The mobile telephone terminal 700 is capable of constantly monitoring the user's breath using the ion mobility sensor 600. Accordingly, by monitoring the chemical substances included in breath, management of the user's health, discovery of the initial state of a disease, monitoring the progress of a disease and the like are possible.

Note that the examples described above are examples of apparatuses and systems to which a transfer apparatus has been applied and the transfer apparatus can be widely used in applications that require the selecting and conveying of trace constituents.

The invention claimed is:

1. An apparatus comprising a transfer device that transfers ionized substances;
   the transfer device comprising:
   a plurality of ring-shaped first electrodes disposed in a line in a first direction, with voltages of different polarities being applied to adjacent electrodes of the plurality of first electrodes, to form a plurality of first alternating current electric fields for linear driving that causes at least some of the ionized substances to travel in the first direction;
   a plurality of second electrodes that are disposed outside the plurality of first electrodes, are aligned in a second direction that is perpendicular to the first direction, and form at least part of a flow path of the ionized substances, the plurality of second electrodes forming a common second alternating current electric field in a direction that is perpendicular to the plurality of first alternating current electric fields formed by the plurality of first electrodes and forming the second alternating current electric field that is asymmetric and deflects a direction of travel of the at least some of the ionized substances in the second direction;

the apparatus further comprises:
- an ionization unit that ionizes one or more substances introduced into the transfer device;
- a detector that detects one or more substances ejected from the transfer device; and
- an accumulator that accumulates one or more substances within the transfer device;

wherein the transfer device further includes:
- a first unit that can deliver the one or more substances to the accumulator;
- a second unit that can deliver the one or more substances to the detector; and
- a bent unit that connects the first unit and the second unit.

2. The apparatus according to claim 1, wherein the plurality of second electrodes include two facing electrodes that form a cylindrical flow path and the plurality of first electrodes are disposed along a center axis of the cylindrical flow path.

3. The apparatus according to claim 1, wherein the second alternating current electric field includes an alternating current component and a direct current component.

4. The apparatus according to claim 1, further comprising a feedback path supplying the one or more substances inside the accumulator from the accumulator to an inlet side of the transfer device.

5. The apparatus according to claim 1 further comprising:
- a plurality of transfer devices-according to claim 1;
- a reaction chamber that accumulates the one or more substances ejected from the plurality of transfer device; and
- an energy supplying unit supplying reaction energy to the one or more substances inside the reaction chamber via an electric field or light.

6. A mobile terminal including the apparatus according to claim 1.

7. The apparatus according to claim 1, wherein the transfer unit is configured such that the electric fields of the first unit, the second unit and the bent unit are formed separately.

8. A method of controlling the apparatus according to claim 1, the method comprising:
- accumulating a substance via the first unit into the accumulator; and
- delivering a substance via the first unit, the bent unit, and the second unit to the detector.

9. The method according to claim 8, wherein the apparatus further includes a feedback path supplying a substance inside the accumulator from the accumulator to an inlet side of the first unit,
the method further comprising concentrating the substance via the feedback path, the first unit and the accumulator.

10. The apparatus according to claim 1, further comprising a feedback path connecting the accumulator to an inlet side of the transfer device.

11. The apparatus according to claim 1, wherein the accumulator is located between the first unit and the bent unit.

12. The apparatus according to claim 11, wherein the first unit is linear.

13. The apparatus according to claim 1, wherein adjacent ones of the first electrodes are separated from each other by an insulator.

* * * * *